US012714394B2

(12) United States Patent
Arai et al.

(10) Patent No.: US 12,714,394 B2
(45) Date of Patent: Aug. 25, 2026

(54) ULTRASONIC PROBE AND ULTRASONIC SYSTEM

(71) Applicant: SEIKO EPSON CORPORATION, Tokyo (JP)

(72) Inventors: Yoshio Arai, Shiojiri (JP); Chikara Kojima, Matsumoto (JP); Hiroto Tomioka, Shiojiri (JP); Keita Kubo, Matsumoto (JP)

(73) Assignee: SEIKO EPSON CORPORATION (JP)

( * ) Notice: Subject to any disclaimer, the term of this patent is extended or adjusted under 35 U.S.C. 154(b) by 62 days.

(21) Appl. No.: 18/344,082

(22) Filed: Jun. 29, 2023

(65) Prior Publication Data

US 2024/0000423 A1 Jan. 4, 2024

(30) Foreign Application Priority Data

Jun. 30, 2022 (JP) ................................ 2022-106523

(51) Int. Cl.
*A61B 8/00* (2006.01)

(52) U.S. Cl.
CPC .............. *A61B 8/4236* (2013.01); *A61B 8/54* (2013.01)

(58) Field of Classification Search
CPC ............................ A61B 8/4236; A61B 8/4494
See application file for complete search history.

(56) References Cited

U.S. PATENT DOCUMENTS

2010/0168576 A1 7/2010 Poland et al.
2013/0258802 A1 10/2013 Nakamura et al.
(Continued)

FOREIGN PATENT DOCUMENTS

JP 2006-051105 A 2/2006
JP 2010-528696 A 8/2010
(Continued)

OTHER PUBLICATIONS

FloPatch FP120, Mar. 2020.*
FloPatch FP120 (Year: 2020).*
Flopatch FP120, Mar. 2020, p. 4 (Year: 2020).*

*Primary Examiner* — Serkan Akar
*Assistant Examiner* — Kaitlyn Eunji Kim
(74) *Attorney, Agent, or Firm* — Harness, Dickey & Pierce, P.L.C.

(57) ABSTRACT

An ultrasonic probe is attached to a target to perform ultrasonic measurement. The ultrasonic probe includes: a first substrate including an ultrasonic element array in which a plurality of ultrasonic elements performing at least one of transmission of ultrasonic waves and reception of ultrasonic waves are arranged in an array, the ultrasonic element array being arranged on a first surface of the first substrate; a second substrate facing a second surface opposite to the first surface of the first substrate; and a housing that houses the first substrate and the second substrate therein and is provided with an opening through which the ultrasonic waves pass at a position corresponding to the ultrasonic element array. The second substrate includes a communication unit coupled to the plurality of ultrasonic elements and capable of wirelessly communicating with another terminal device. A weight of the ultrasonic probe is 150 g or less.

12 Claims, 10 Drawing Sheets

(56) References Cited

U.S. PATENT DOCUMENTS

| | | | | |
|---|---|---|---|---|
| 2015/0190118 | A1* | 7/2015 | Kiyose | A61B 8/4483 600/443 |
| 2015/0266058 | A1 | 9/2015 | Yoshida et al. | |
| 2018/0228462 | A1 | 8/2018 | Maghsoudnia et al. | |
| 2019/0038256 | A1 | 2/2019 | Arai et al. | |
| 2020/0166638 | A1* | 5/2020 | Kojima | H10N 30/101 |
| 2022/0000447 | A1* | 1/2022 | Eibl | A61B 8/4494 |

FOREIGN PATENT DOCUMENTS

| | | | |
|---|---|---|---|
| JP | 2013-211604 | A | 10/2013 |
| JP | 6252280 | B2 | 12/2017 |
| JP | 6451216 | B2 | 1/2019 |
| JP | 6939219 | B2 | 9/2021 |

* cited by examiner

FIG. 3

ULTRASONIC PROBE AND ULTRASONIC SYSTEM

The present application is based on, and claims priority from JP Application Serial Number 2022-106523, filed Jun. 30, 2022, the disclosure of which is hereby incorporated by reference herein in its entirety.

BACKGROUND

1. Technical Field

The present disclosure relates to an ultrasonic probe and an ultrasonic system.

2. Related Art

In the related art, there is an ultrasonic probe that performs medical operations such as imaging of an internal tomographic image of a human body and a treatment of a predetermined tissue by transmitting ultrasonic waves to a predetermined site of the human body (for example, JP-A-2013-211604).

The ultrasonic probe described in JP-A-2013-211604 is coupled to a device terminal via a cable. In addition, the ultrasonic probe includes a housing in which an ultrasonic transducer that outputs ultrasonic waves is housed. The housing includes a probe main body and a probe head that is detachable from the probe main body. For such an ultrasonic probe, an operator holds the probe main body by a hand and operates the ultrasonic probe by bringing the probe head into contact with the human body along the skin (surface) of the human body.

However, with regard to the operation of the ultrasonic probe as described in JP-A-2013-211604, it is necessary to appropriately operate the ultrasonic probe with specialized knowledge. While various types of processing using ultrasonic waves are being performed, the operator grips the probe main body of the ultrasonic probe and maintains a posture such that the probe head comes into contact with the skin of a target person. Accordingly, for example, when it is desired to perform measurement processing by the ultrasonic probe over a long period of time, there is also a problem that the operator needs to keep holding the ultrasonic probe at all times, and the ultrasonic probe cannot be easily used.

For this reason, an ultrasonic probe that can be attached to a target for a long period of time is desired.

SUMMARY

An ultrasonic probe according to a first aspect of the present disclosure is an ultrasonic probe that is attached to a target to perform ultrasonic measurement. The ultrasonic probe includes: a first substrate including an ultrasonic element array in which a plurality of ultrasonic elements performing at least one of transmission of ultrasonic waves and reception of ultrasonic waves are arranged in an array, the ultrasonic element array being arranged on a first surface of the first substrate; a second substrate facing a second surface opposite to the first surface of the first substrate; and a housing that houses the first substrate and the second substrate therein and is provided with an opening through which the ultrasonic waves pass at a position corresponding to the ultrasonic element array. The second substrate includes a communication unit coupled to the plurality of ultrasonic elements and capable of wirelessly communicating with another terminal device. A weight of the ultrasonic probe is 150 g or less.

In the ultrasonic probe according to the present aspect, it is preferable that an axis orthogonal to the first surface is defined as a first axis, and a dimension of the housing along the first axis is 10 mm or less.

In the ultrasonic probe according to the present aspect, it is preferable that the second substrate includes a control circuit configured to control the plurality of ultrasonic elements, and the control circuit includes a driver configured to drive the plurality of ultrasonic elements to transmit the ultrasonic waves, and a signal processing unit configured to process a signal to be output when the ultrasonic waves are received by the plurality of ultrasonic elements.

In the ultrasonic probe according to the present aspect, it is preferable that an acoustic lens, which converges the ultrasonic waves output from the ultrasonic element array to a predetermined depth, is provided in the opening of the housing.

An ultrasonic system according to a second aspect of the present disclosure includes: the ultrasonic probe described above; and a terminal device communicably connected via the communication unit.

BRIEF DESCRIPTION OF THE DRAWINGS

FIG. 3 is a schematic cross-sectional view of the ultrasonic probe taken along a line A-A in FIG. 2.

DESCRIPTION OF EXEMPLARY EMBODIMENTS

Hereinafter, an embodiment of the present disclosure will be described.

Figure 1:
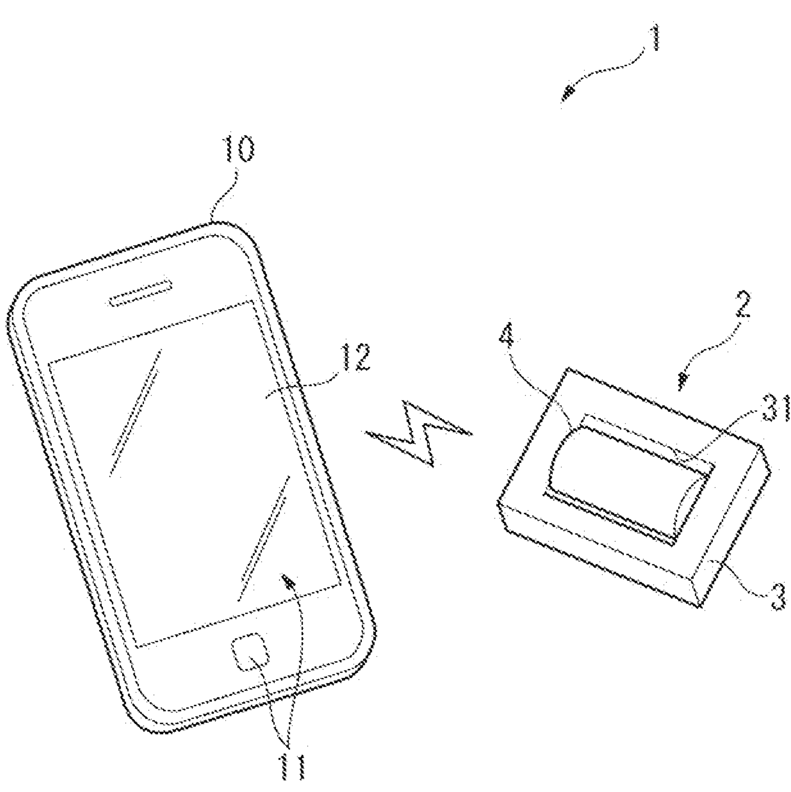
FIG. 1 is a schematic perspective view showing an ultrasonic probe and an ultrasonic system according to an embodiment of the present disclosure.

FIG. 1 is a schematic diagram showing an ultrasonic probe and an ultrasonic system according to the present embodiment.

As shown in FIG. 1, an ultrasonic system 1 includes an ultrasonic probe 2 and a terminal device 10 communicably connected to the ultrasonic probe 2.

The ultrasonic system 1 transmits ultrasonic waves from the ultrasonic probe 2 into a human body in a state where the ultrasonic probe 2 is in contact with a surface of a target (for example, the human body in the present embodiment). In addition, the ultrasonic probe 2 receives ultrasonic waves reflected by an organ in a living body, and based on the reception signal, for example, obtains an internal tomographic image in the living body, measures the state of the organ in the living body (for example, blood flow), or performs treatment by converging the ultrasonic waves on a predetermined organ.

1. Configuration of Terminal Device 10

As shown in FIG. 1, the terminal device 10 includes an operation unit 11, which includes a button, a touch panel, and the like, and a display unit 12. Although not shown, the terminal device 10 includes a storage unit implemented by a memory and the like, and a calculation unit implemented by a central processing unit (CPU) and the like. The terminal device 10 controls the ultrasonic system 1 by causing the calculation unit to execute various programs stored in the storage unit. For example, the terminal device 10 outputs a command for controlling the driving of the ultrasonic probe 2, and based on an ultrasonic signal received from the ultrasonic probe 2, forms an image of an internal structure of the living body and causes the display unit 12 to display the image, or measures biological information such as a blood flow and causes the display unit 12 to display the biological information. As such a terminal device 10, for example, a terminal device such as a tablet terminal, a smartphone, or a personal computer can be used, and a dedicated terminal device for operating the ultrasonic probe 2 may be used.

2. Configuration of Ultrasonic Probe 2

Figure 2:
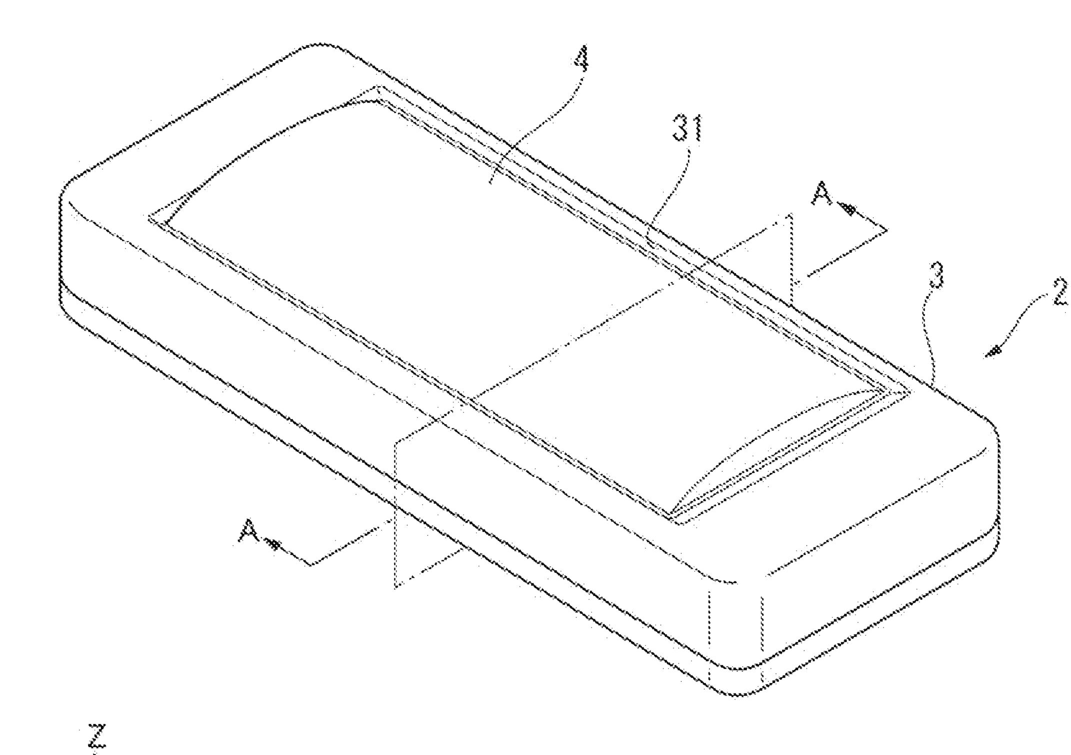
FIG. 2 is a perspective view showing an external appearance of the ultrasonic probe according to the present embodiment.
Figure 2:
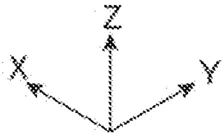
Figure 3:
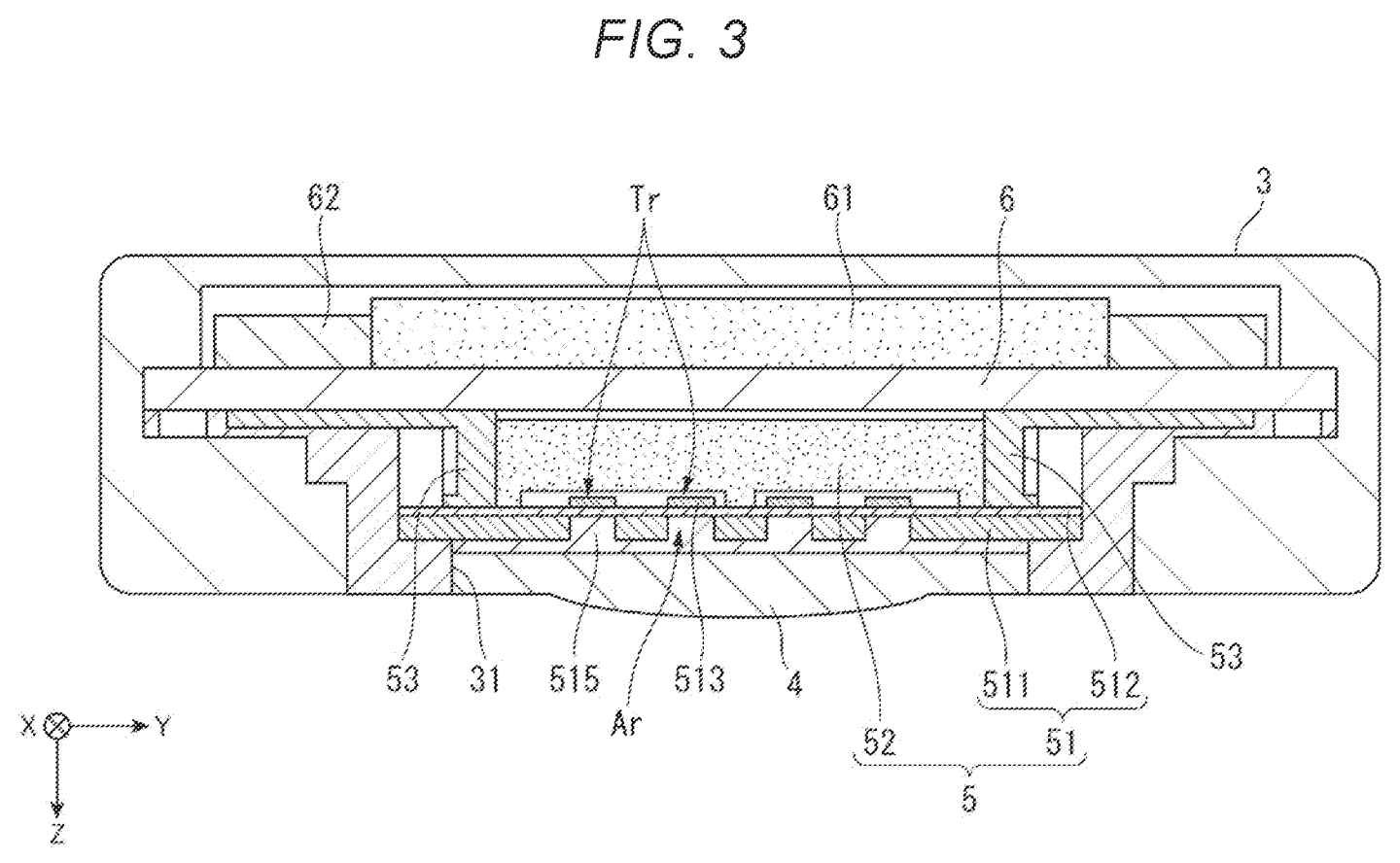

FIG. 2 is a perspective view showing an external appearance of the ultrasonic probe 2. FIG. 3 is a schematic cross-sectional view of the ultrasonic probe 2 when the ultrasonic probe 2 is cut along a line A-A in FIG. 2.

As shown in FIGS. 2 and 3, the ultrasonic probe 2 includes a housing 3, an acoustic lens 4, which is disposed in an opening 31 provided in the housing 3 and is exposed to the outside, a first substrate 5 and a second substrate 6 housed in the housing 3, and the like.

2-1. Configuration of First Substrate 5

The first substrate 5 is a substrate facing the opening 31 provided in the housing 3. The first substrate includes an ultrasonic substrate 51 and a device substrate 52. The ultrasonic substrate 51 is disposed closer to the opening 31 than the device substrate 52 and is bonded to the device substrate 52. That is, the ultrasonic substrate 51 constitutes a first surface of the first substrate 5 facing the opening 31.

2-1-1. Configuration of Ultrasonic Substrate 51

Figure 4:
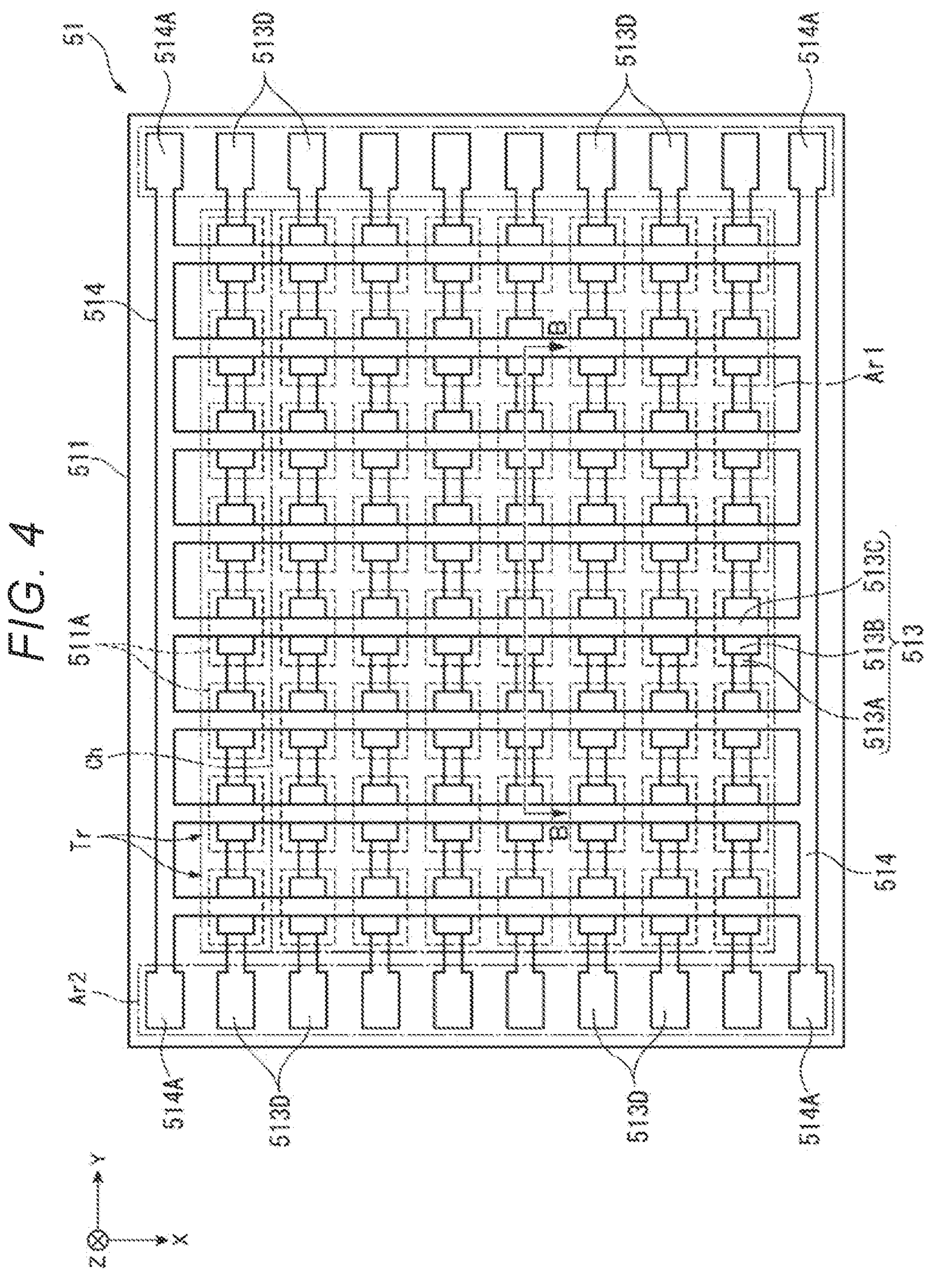
FIG. 4 is a plan view showing a schematic configuration of an ultrasonic substrate according to the present embodiment.
Figure 5:
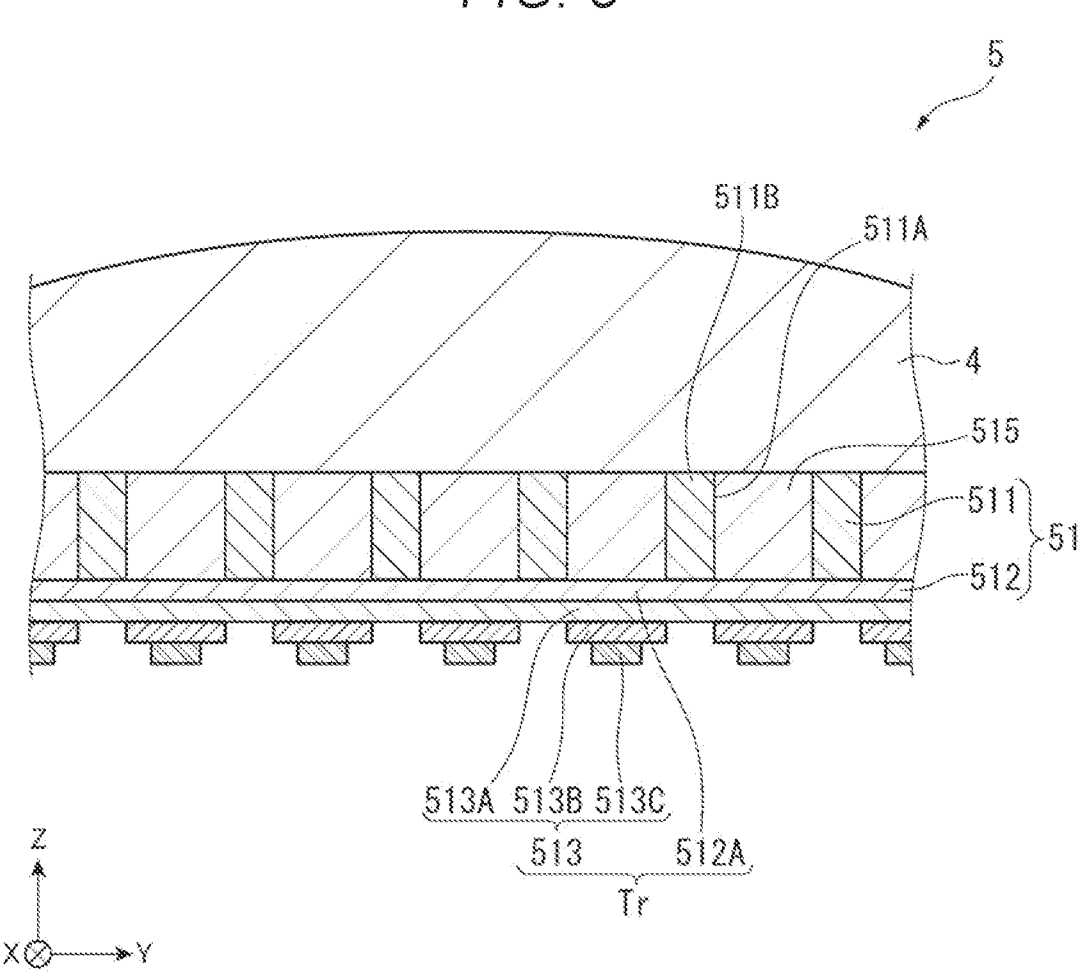
FIG. 5 is a schematic cross-sectional view of the ultrasonic substrate taken along a line B-B in FIG. 4.

FIG. 4 is a plan view showing a schematic configuration of the ultrasonic substrate 51 according to the present embodiment. FIG. 5 is a schematic cross-sectional view of the ultrasonic substrate 51 taken along a line B-B in FIG. 4.

As shown in FIG. 4, a plurality of ultrasonic elements (ultrasonic transducers Tr) are arranged in a two-dimensional array on the ultrasonic substrate 51 along an X direction and a Y direction. Here, a direction orthogonal to the X direction and the Y direction is a Z direction, and a Z axis parallel to the Z direction corresponds to a first axis of the present disclosure.

In the present embodiment, a transmission and reception column Ch (vibrator) of 1 CH (channel) is constituted by the plurality of ultrasonic transducers Tr arranged in the Y direction. In addition, an ultrasonic element array Ar having a one-dimensional array structure is constituted by arranging a plurality of the transmission and reception columns Ch of 1 CH along the Y direction.

In FIG. 4, the arrangement number of the ultrasonic transducers Tr is reduced for convenience of description, and more ultrasonic transducers Tr may be actually arranged.

As shown in FIG. 5, the ultrasonic substrate 51 includes an element substrate 511, a vibration plate 512 provided on the element substrate 511, and piezoelectric elements 513 provided on the vibration plate 512.

The element substrate 511 is implemented by, for example, a semiconductor substrate made of Si. The element substrate 511 is provided with substrate opening portions 511A respectively corresponding to the ultrasonic transducers Tr. In the present embodiment, each substrate opening portion 511A is a through hole penetrating the element substrate 511 in a substrate thickness direction (Z direction), and the vibration plate 512 is provided on a −Z side (device substrate 52 side) of the through hole.

A side (+Z) of the substrate opening portion 511A where the vibration plate 512 is not provided is filled with an acoustic layer 515 having an acoustic impedance close to that of the living body. As the acoustic layer 515, for example, a resin material such as silicone can be used.

The acoustic lens 4 is provided on the +Z side of the element substrate 511. The acoustic lens 4 may be in contact with the element substrate 511, and the acoustic layer 515 may be interposed between the acoustic lens 4 and the element substrate 511. As described above, the acoustic lens 4 is exposed from the opening 31 of the housing 3, and is a portion that comes into contact with the human body when the ultrasonic measurement is performed. Similarly to the acoustic layer 515, the acoustic lens 4 is made of, for example, silicone having an acoustic impedance close to that of the living body, and is formed in a cylindrical shape with the X direction as an axis.

The vibration plate 512 is formed of, for example, a stacked body of $SiO_2$ and $ZrO_2$, and covers the entire device substrate 52 side of the element substrate 511. That is, the vibration plate 512 is supported by partition walls 511B constituting the substrate opening portions 511A and closes the −Z side of the substrate opening portions 511A. A thickness of the vibration plate 512 is sufficiently smaller than that of the element substrate 511.

The piezoelectric elements 513 are provided on the vibration plate 512 that closes the substrate opening portions 511A. The piezoelectric element 513 includes, for example, a stacked body in which a lower electrode 513A, a piezoelectric film 513B, and an upper electrode 513C are stacked from the vibration plate 512 toward the −Z side.

Here, a portion of the vibration plate 512 that closes the substrate opening portion 511A constitutes a vibration portion 512A, and the vibration portion 512A and the piezoelectric element 513 constitute one ultrasonic transducer Tr.

In such an ultrasonic transducer Tr, when a rectangular wave voltage (drive signal) having a predetermined frequency is applied between the lower electrode 513A and the upper electrode 513C, the piezoelectric film 513B is bent, the vibration portion 512A vibrates, and ultrasonic waves are transmitted to the +Z side. When the vibration portion 512A is vibrated by the ultrasonic waves (reflected waves) reflected from the living body, a potential difference is generated between the upper and lower sides of the piezoelectric film 513B. Accordingly, the received ultrasonic waves can be detected by detecting a potential difference generated between the lower electrode 513A and the upper electrode 513C.

In the present embodiment, as shown in FIG. 4, the lower electrode 513A is formed in a linear shape along the Y direction, and couples the plurality of ultrasonic transducers Tr constituting the transmission and reception column Ch of 1 CH. A drive terminal 513D is electrically coupled to a wiring circuit of the second substrate 6 through, for example, a flexible print substrate 53 (see FIG. 3).

The upper electrode 513C is formed in a linear shape along the X direction, and couples the ultrasonic transducers Tr arranged in the X direction. End portions on the ±X sides of the upper electrode 513C is coupled to a common electrode line 514. The common electrode line 514 couples a plurality of the upper electrodes 513C arranged along the Y direction, and a common terminal 514A electrically coupled to the wiring circuit of the second substrate 6 is provided at one end portion of the common electrode line 514. The common terminal 514A is electrically coupled to the second substrate 6 by, for example, the flexible print substrate 53 (see FIG. 3).

FIG. 3 shows an example in which the drive terminal 513D and the common terminal 514A are coupled to the second substrate 6 by the flexible print substrate 53, and for example, coupling by a lead wire may be used, or coupling using a through electrode provided in the device substrate 52 may be used.

In the present embodiment, an example in which the ultrasonic element array Ar having a one-dimensional array structure is formed on the ultrasonic substrate 51 is shown, and an ultrasonic element array having a two-dimensional array structure may be formed by individually driving the ultrasonic transducers Tr arranged in the X direction and the ultrasonic transducers Tr arranged in the Y direction.

2-1-2. Configuration of Device Substrate 52

The device substrate 52 and the ultrasonic substrate 51 constitute the first substrate 5, and the device substrate 52 is bonded to a surface of the ultrasonic substrate 51 on the −Z side facing the opening 31. That is, a surface of the device substrate 52 on the −Z side constitutes a second surface of the first substrate 5 opposite to the first surface.

The device substrate 52 is bonded to the vibration plate 512 side of the ultrasonic substrate 51, by a fixing member such as a resin, at positions overlapping the partition walls 511B when viewed from the substrate thickness direction to reinforce the ultrasonic substrate 51.

2-2. Configuration of Second Substrate 6

The second substrate 6 is disposed on the −Z side of the first substrate 5. As described above, the drive terminal 513D and the common terminal 514A are coupled to the second substrate 6 by the flexible print substrate 53.

Figure 6:
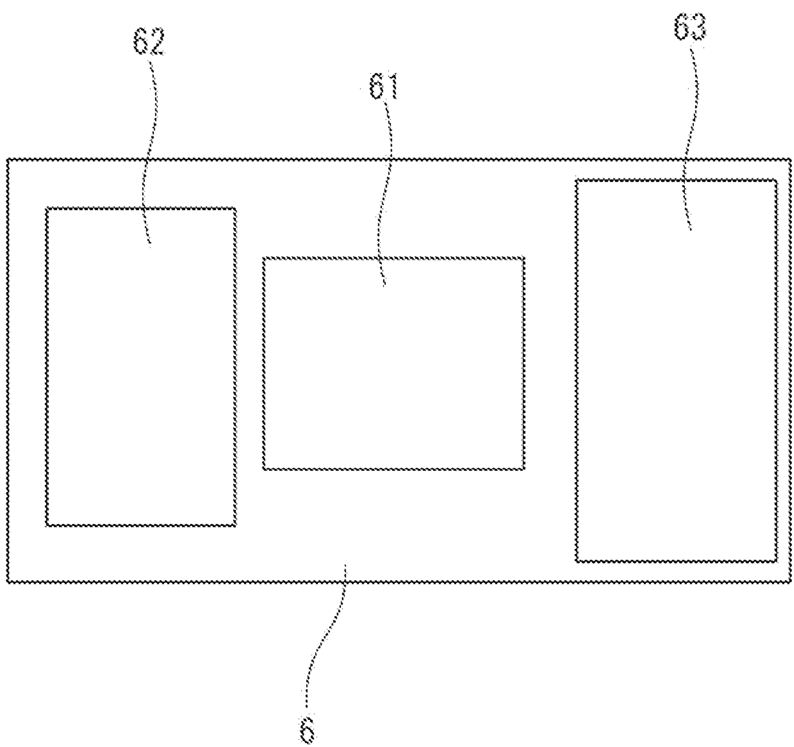
FIG. 6 is a diagram showing an arrangement example of each configuration when a second substrate according to the present embodiment is viewed from a −Z side.

FIG. 6 is a diagram showing an arrangement example of each configuration when the second substrate 6 is viewed from the −Z side.

As shown in FIG. 6, an IC chip 61, a communication unit 62, and a battery arrangement unit 63 are provided on a surface of the second substrate 6 on the −Z side. FIG. 6 shows an example in which one IC chip 61 is provided for simplification of description, and a plurality of the IC chips 61 may be provided. One or more IC chips 61 constitute a control circuit 80 (see FIG. 10).

The IC chip 61 and the second substrate 6 may be coupled to each other by bonding, for example, soldering terminal legs of the IC chip 61 to a print circuit (wiring circuit) formed on the second substrate 6.

Alternatively, a bare chip may be used as the IC chip 61, and in this case, the bare chip and the print circuit (wiring circuit) formed on the second substrate 6 may be coupled by wire bonding and the like. When the bare chip is used, a package housing of the IC chip is not required, and thus the thickness can be further reduced.

The communication unit 62 is coupled to the IC chip 61 and the drive terminal 513D via the wiring circuit, and communicates with the terminal device 10 by wireless communication. A communication method of the communication unit 62 is not particularly limited, and for example, Bluetooth (registered trademark), an infrared ray, and a wireless LAN can be used.

A battery is disposed in the battery arrangement unit 63. As the battery, for example, a rechargeable battery can be used.

In the present embodiment, the IC chip 61, the communication unit 62, and the battery arrangement unit 63 are disposed in the same plane on the surface of the second substrate 6 on the −Z side, and do not overlap in the Z direction.

3. Configuration of Housing 3 and Attachment of Ultrasonic Probe 2 to Human Body The housing 3 has the opening 31 on one surface on the +Z side, and the acoustic lens 4 exposed from the opening 31 is provided in the housing 3. The first substrate 5, the second substrate 6, and the like are disposed inside the housing 3, and the first substrate 5 and the second substrate 6 are stacked from the +Z side toward the −Z side.

In the housing 3 having such a configuration, the dimension in the thickness direction (Z direction) can be minimized, and the ultrasonic probe 2 can be downsized. Specifically, the thickness of the housing 3 in the Z direction is 10 mm or less.

As described above, by setting the thickness of the housing 3 to 10 mm or less, when the ultrasonic probe 2 is attached to the human body, the ultrasonic probe 2 can be accommodated in a gap between a skin surface and clothes without giving the user a feeling of discomfort.

In the present embodiment, a shape of the housing 3 viewed from the Z direction is formed in a substantially rectangular shape. The rectangular housing 3 having a short axis and a long axis is shown as an example, and the housing 3 may have, for example, an elliptical shape or a polygonal shape, or may have a square shape. Here, it is preferable that a length of the housing 3 in a long axis direction (a long side in a rectangular shape) is 50 mm or less and a length of the housing 3 in a short axis direction is 15 mm or more in a plan view from the Z direction of the housing 3.

The surface of the human body has many curved surfaces. When the length of the housing 3 in the long axis direction has a size exceeding 50 mm, it is difficult for an ultrasonic wave passing surface including the acoustic lens 4 exposed from the opening 31 to uniformly adhere to the human body. By setting the length in the long axis direction to 50 mm or less, it is possible to uniformly adhere to the surface of the human body, and for example, when an internal tomographic image of the inside of the human body is to be captured, it is possible to appropriately transmit ultrasonic waves to a desired range.

When the length of the housing 3 in the short axis direction is less than 15 mm, an area of the ultrasonic element array Ar housed in the housing 3 is also reduced. In this case, the measurable range and depth, and a sound pressure of the ultrasonic waves are also reduced. On the other hand, by setting the length of the housing 3 in the short axis direction to 15 mm or more, it is possible to expose the ultrasonic element array Ar having a size capable of performing appropriate measurement from the opening 31 of the housing 3.

Figure 7:
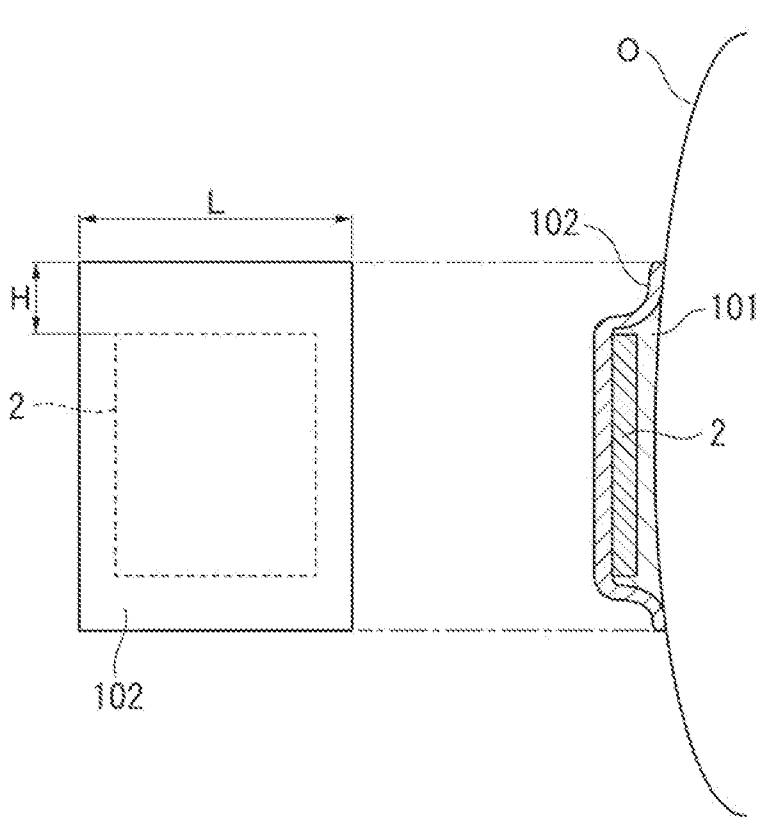
FIG. 7 is a diagram showing an attachment example of the ultrasonic probe according to the present embodiment to a human body.

FIG. 7 is a diagram showing an attachment example of the ultrasonic probe 2 according to the present embodiment to the human body.

As shown in FIG. 7, in the ultrasonic probe 2 according to the present embodiment, when a gel 101 for matching the acoustic impedance is interposed between the ultrasonic probe 2 and a human body O, the ultrasonic probe 2 is adhered to the human body O, and the ultrasonic probe 2 is attached to the human body O using a medical tape 102.

An adhesive force of the medical tape 102 is generally set such that the medical tape 102 can be attached and detached without damaging the skin.

When the ultrasonic probe 2 is fixed to the human body O by using the medical tape 102, a peeling strength of the tape changes depending on an attachment length H of the medical tape 102 stretched to the outside of the ultrasonic probe 2 and a width L (see FIG. 7) of the medical tape 102.

In the fixing of the ultrasonic probe 2 using such a medical tape 102, it is preferable to reduce an attachment area to the human body as much as possible and to reduce a length of the tape. Accordingly, stimulation to the skin by the medical tape 102 can be reduced, and a tape cost can be reduced. In order to shorten the length of the tape, a width direction of the medical tape 102 is aligned with the long axis direction of the housing 3, and the medical tape 102 is stretched along the short axis direction of the housing 3 and attached.

In the present embodiment, the length of the housing 3 of the ultrasonic probe 2 in the long axis direction is 50 mm or less, and the length in the short axis direction is 15 mm or more. Accordingly, in the medical tape 102, the width L of the tape is preferably set to 50 mm or more corresponding to the long axis of the housing 3.

Figure 8:
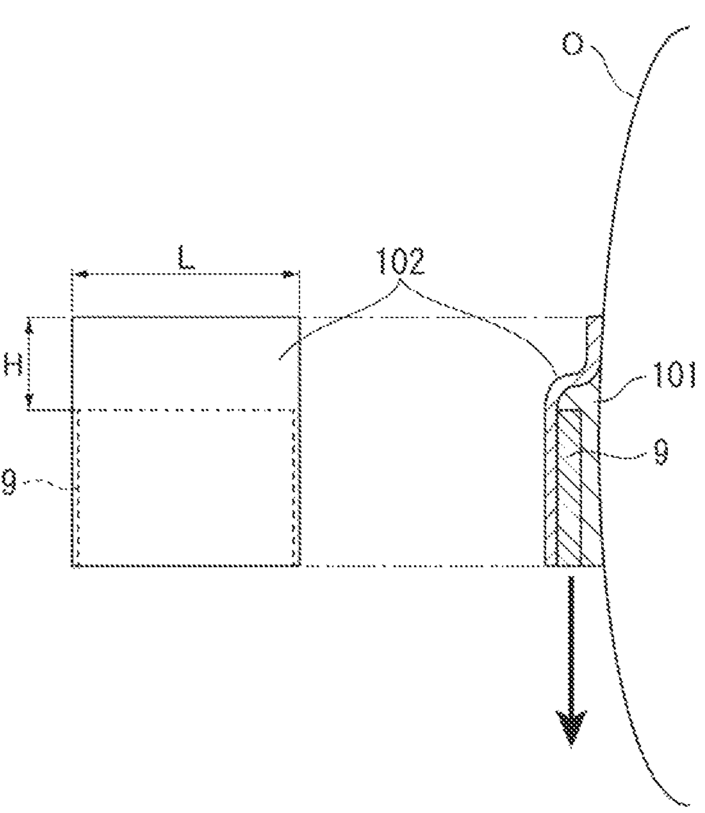
FIG. 8 is a diagram showing an experimental example in which a tape strength of a medical tape 102 is measured.
Figure 9:
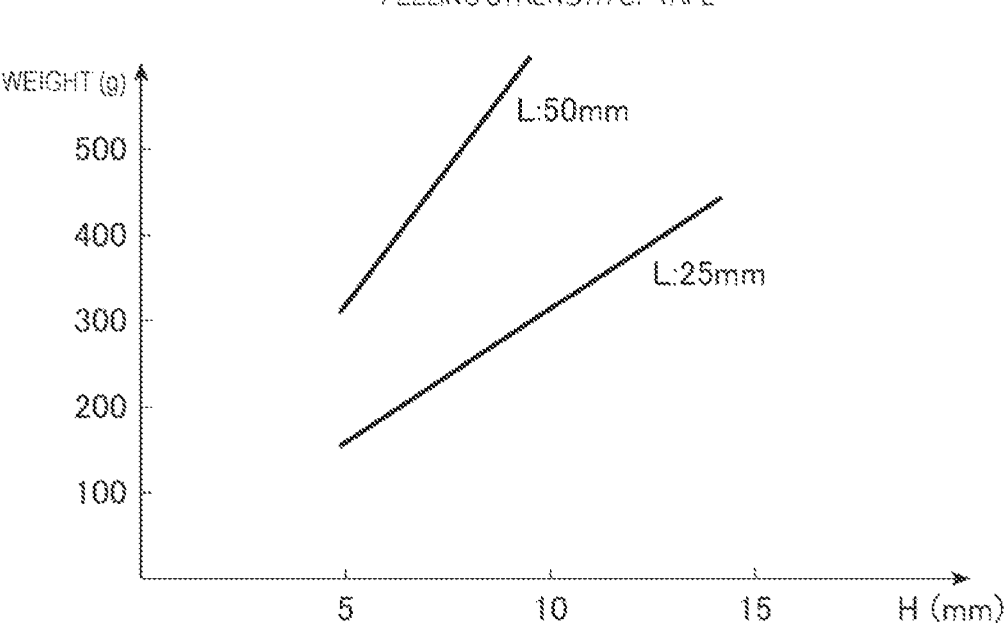
FIG. 9 is a diagram showing the strength of the medical tape 102.

FIG. 8 is a diagram showing an experimental example in which a tape strength of the medical tape 102 is measured. FIG. 9 is a diagram showing the result, that is, the strength of the medical tape 102.

That is, when a weight body 9 having the same shape as the ultrasonic probe 2 according to the present embodiment is attached to the human body O using the medical tape 102, the attachment length H of the medical tape 102 in the short axis direction is changed, and the attachment length H from which the weight body 9 drops is measured. By performing the experiment a plurality of times while changing a weight (load) of the weight body 9, a relationship diagram as shown in FIG. 9 is obtained.

In the present embodiment, the ultrasonic probe 2 is formed to have a total weight of 150 g or less. In this case, as shown in FIG. 9, even when the attachment length H of the medical tape 102 is about 5 mm, the dropping of the ultrasonic probe 2 can be prevented.

That is, since the total weight of the ultrasonic probe 2 according to the present embodiment is 150 g or less, it is possible to reduce the attachment area of the medical tape 102 to the human body O and to prevent the influence on the skin of the human body O. Even when the attachment length H of the medical tape 102 is set to a short dimension of 5 mm to 10 mm, the dropping of the ultrasonic probe 2 can be prevented, the attachment length H can be shortened, and thus the cost can be reduced.

4. System Configuration of Ultrasonic System 1

Next, a system configuration of the ultrasonic system 1 according to the present embodiment will be described.

Figure 10:
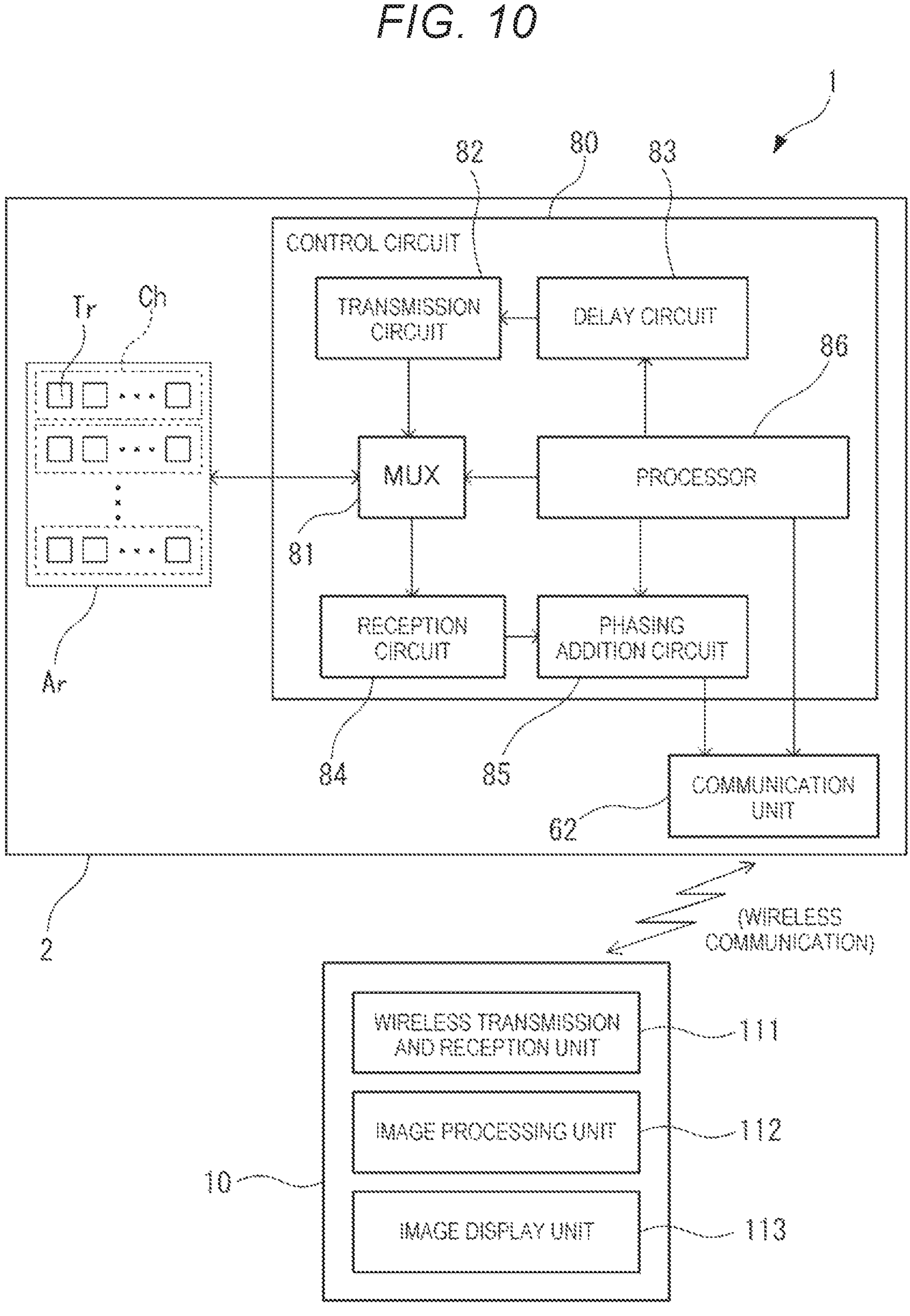
FIG. 10 is a block diagram of the ultrasonic system according to the present embodiment.

FIG. 10 is a block diagram of the ultrasonic system 1 according to the present embodiment.

In the present embodiment, as described above, the control circuit 80 is implemented by the plurality of IC chips 61 of the second substrate 6. As shown in FIG. 10, the control circuit 80 includes a multiplexer (MUX 81), a transmission circuit 82, a delay circuit 83, a reception circuit 84, a phasing addition circuit 85, and a processor 86.

The MUX 81 is coupled to each ultrasonic transducer Tr of the ultrasonic element array Ar, the transmission circuit 82, and the reception circuit 84. The MUX 81 is controlled based on a drive switching signal from the processor 86, and switches between transmission coupling that couples the ultrasonic transducer Tr and the transmission circuit 82 and reception coupling that couples the ultrasonic transducer Tr and the reception circuit 84.

During the transmission coupling, the transmission circuit 82 outputs a drive signal having a predetermined drive voltage to each ultrasonic transducer Tr to cause each ultrasonic transducer Tr to transmit ultrasonic waves.

The delay circuit 83 is controlled by the processor 86 and sets an output timing of the drive signal output from the transmission circuit 82 to each ultrasonic transducer Tr. In the present embodiment, the transmission and reception column Ch of 1 CH is implemented by the plurality of ultrasonic transducers Tr, and the ultrasonic waves transmitted from the transmission and reception column Ch of 1 CH are converged to a predetermined depth by the acoustic lens 4. By driving a plurality of the transmission and reception columns Ch with delay by the delay circuit 83, an ultrasonic beam can be oscillated in the X direction, and ultrasonic measurement capable of measuring an internal tomographic image in a plane along an XZ plane can be performed.

The transmission circuit 82 and the delay circuit 83 constitute a driver of the present disclosure.

The reception circuit 84 processes a reception signal output from each channel during the reception coupling under the control of the processor 86. For example, AD conversion processing is performed after amplifying a signal strength of the reception signal.

Under the control of the processor 86, the phasing addition circuit 85 performs phasing addition processing on the reception signal output from the reception circuit 84 and outputs an ultrasonic signal.

The reception circuit 84 and the phasing addition circuit 85 constitute a signal processing unit of the present disclosure.

The processor 86 controls operations of the circuits, communicates with the terminal device 10 by controlling the communication unit 62, and transmits and receives various types of information.

Specifically, by receiving a measurement command from the terminal device 10 to perform the ultrasonic measurement, the processor 86 controls the transmission circuit 82, the delay circuit 83, the reception circuit 84, and the phasing addition circuit 85, and performs the ultrasonic measurement by the ultrasonic probe 2. Then, the processor 86 transmits, from the communication unit 62 to the terminal device 10, the ultrasonic signal output from the phasing addition circuit 85.

The terminal device 10 functions as, for example, a wireless transmission and reception unit 111, an image processing unit 112, and an image display unit 113 as shown in FIG. 10, by the calculation unit executing various programs stored in the storage unit.

Based on an operation and the like of a user, the wireless transmission and reception unit 111 transmits a measurement command signal to the ultrasonic probe 2 and receives an ultrasonic signal from the ultrasonic probe 2.

The image processing unit 112 generates an internal tomographic image of a target (human body) based on the obtained ultrasonic signal.

The image display unit 113 causes the display unit 12 to display the generated internal tomographic image.

5. Functions and Effects of Embodiment

The ultrasonic probe 2 according to the present embodiment includes: the first substrate 5 including the ultrasonic element array Ar in which the plurality of ultrasonic transducers Tr for transmitting and receiving ultrasonic waves are arranged in an array, the ultrasonic element array Ar being arranged on the first surface of the first substrate 5 (surface on the +Z side); the second substrate 6 facing the second surface (surface on the −Z side) opposite to the first surface of the first substrate and the housing 3 that houses the first substrate 5 and the second substrate 6 therein and is provided with the opening 31 through which the ultrasonic waves pass at a position corresponding to the ultrasonic element array Ar. The second substrate 6 includes the communication unit 62 coupled to the plurality of ultrasonic transducers Tr and capable of wirelessly communicating with the terminal device 10. A weight of the ultrasonic probe 2 is 150 g or less.

In such an ultrasonic probe 2, when the ultrasonic probe 2 is attached to the human body using the medical tape 102, peeling of the medical tape 102 due to the weight of the ultrasonic probe 2 can be prevented.

In particular, when the ultrasonic probe 2 is attached to the human body, in order to appropriately adhere the transmission part of the ultrasonic waves to the human body, it is preferable that the length of the housing 3 in the long axis direction is 50 mm or less. In addition, in order to perform appropriate ultrasonic measurement, it is preferable to perform beam forming using a sufficient number of ultrasonic transducers Tr, and it is preferable that the length of the housing 3 in the short axis direction is 15 mm or more. When such an ultrasonic probe 2 is attached to the human body, in order to reduce an attachment amount of the medical tape 102 as much as possible, the medical tape 102 is stretched along the short axis direction to attach the housing 3 to the human body. At this time, in the present embodiment, since the weight of the ultrasonic probe 2 is 150 g or less, it is possible to prevent the ultrasonic probe 2 from falling off only by stretching the medical tape 102 by about 5 mm to the outer side of the housing 3 and attaching the medical tape 102 to the human body.

Since the ultrasonic probe 2 is configured to communicate with the terminal device 10 by wireless communication through the communication unit 62, the ultrasonic probe 2 is not connected by wire. Therefore, even when the ultrasonic probe 2 is attached for a long period of time, there is no inconvenience caused by a wire, and there is no inconvenience caused by peeling off of the medical tape 102 due to a wire being caught.

In the ultrasonic probe 2 according to the present embodiment, the dimension (thickness) of the housing 3 along the Z direction is 10 mm or less.

Accordingly, even when the ultrasonic probe 2 is attached to the human body, the ultrasonic probe 2 can sufficiently enter between the human body and the clothes. Accordingly, even when the ultrasonic probe 2 is attached to the human body for a long period of time, it is possible to prevent the inconvenience of a trouble in usual life.

In the ultrasonic probe 2 according to the present embodiment, the second substrate 6 includes the control circuit 80 that controls the plurality of ultrasonic transducers Tr, and the control circuit 80 includes the transmission circuit 82 and the delay circuit 83 that drive the plurality of ultrasonic elements to transmit ultrasonic waves. In addition, the control circuit 80 includes the reception circuit 84 and the phasing addition circuit 85 that process signals output when the plurality of ultrasonic transducers Tr receive the ultrasonic waves.

Accordingly, the terminal device 10 communicably connected to the ultrasonic probe 2 only needs to output a measurement command to the ultrasonic probe 2 to perform ultrasonic measurement, receive the ultrasonic signal obtained from the ultrasonic probe 2, and form an image. That is, in the terminal device 10, a circuit for focusing an ultrasonic beam, a circuit for performing phasing addition processing of reception signals, and the like are unnecessary, and the ultrasonic system 1 can be constructed by a general-purpose computer such as a smartphone or a tablet terminal.

In the ultrasonic probe 2 according to the present embodiment, the acoustic lens 4 that converges, to a predetermined depth, the ultrasonic waves output from the ultrasonic element array Ar is provided in the opening 31 of the housing 3.

Accordingly, it is possible to easily form an ultrasonic beam that converges from the transmission and reception column Ch of 1 Ch to a predetermined depth.

The ultrasonic system 1 according to the present embodiment includes the ultrasonic probe 2 and the terminal device 10 communicably connected to the ultrasonic probe 2 via the communication unit 62.

Accordingly, the ultrasonic probe 2 and the terminal device 10 can wirelessly communicate with each other, and the user can check a measurement result on the terminal device 10 during the ultrasonic measurement. At this time, since the ultrasonic probe 2 and the terminal device 10 are not coupled to each other by wire, it is possible to prevent an inconvenience caused by falling off of the ultrasonic probe 2 due to wire catching and the like or a wire becomes an obstacle during the attachment of the ultrasonic probe 2.

Modification

The present disclosure is not limited to the embodiments described above and modifications, and configurations obtained through modifications, alterations, and appropriate combinations of the embodiments within a scope of being capable of achieving the object of the present disclosure are included in the present disclosure.

In the above embodiment, the ultrasonic element array Ar has a one-dimensional array structure in which the plurality of transmission and reception columns Ch are arranged in the X direction. An ultrasonic element array having a two-dimensional array structure in which the plurality of ultrasonic transducers Tr that can be independently driven are arranged in the X direction and the Y direction may be constructed. In this case, the acoustic lens 4 can be eliminated.

In the above embodiment, the control circuit 80 provided in the ultrasonic probe 2 includes the transmission circuit 82, the delay circuit 83, the reception circuit 84, and the phasing addition circuit 85, and is configured to transmit the ultrasonic signal to the terminal device 10. In response to this, the processor 86 may further form an image based on the ultrasonic signal and transmit the generated image to the terminal device 10.

In the above embodiment, each ultrasonic transducer Tr performs transmission and reception of ultrasonic waves, and for example, may perform only transmission of ultrasonic waves. That is, in the ultrasonic system 1, the internal tomographic image of the human body is obtained by the ultrasonic measurement performed by the ultrasonic probe 2. By transmitting the ultrasonic waves to a predetermined site (for a predetermined period) of the human body, the ultrasonic system 1 may be caused to function as an ultrasonic treatment device that performs treatment of the site. In this case, reception processing of the ultrasonic waves is unnecessary, and the reception circuit 84 and the phasing addition circuit 85 can be unnecessary.

In the above embodiment, the example in which the ultrasonic probe 2 is attached to the human body is shown, and the ultrasonic probe 2 may be attached to another target. Examples of the target to which the ultrasonic probe 2 is attached include a living body such as a pet and an inorganic substance such as a concrete structure.

Summary of Present Disclosure

An ultrasonic probe according to a first aspect of the present disclosure is an ultrasonic probe that is attached to a target to perform ultrasonic measurement. The ultrasonic probe includes: a first substrate including an ultrasonic element array in which a plurality of ultrasonic elements performing at least one of transmission and reception of ultrasonic waves are arranged in an array, the ultrasonic element array being arranged on a first surface of the first substrate; a second substrate facing a second surface opposite to the first surface of the first substrate; and a housing that houses the first substrate and the second substrate therein and is provided with an opening through which the ultrasonic waves pass at a position corresponding to the ultrasonic element array. The second substrate includes a communication unit coupled to the plurality of ultrasonic elements and capable of wirelessly communicating with another terminal device. A weight of the ultrasonic probe is 150 g or less.

In the ultrasonic probe having such a configuration, when the ultrasonic probe is attached to a target such as a human body using a general medical tape, peeling of the medical tape due to a weight of the ultrasonic probe is prevented, and the ultrasonic probe can be attached to the target over a long period of time. In addition, since a wire is not used for coupling to the terminal device, it is possible to prevent falling off and the like of the ultrasonic probe due to wire catching.

In the ultrasonic probe according to the present aspect, it is preferable that an axis orthogonal to the first surface is defined as a first axis, and a dimension of the housing along the first axis is 10 mm or less.

Accordingly, even when the ultrasonic probe is attached to the human body, the ultrasonic probe can sufficiently enter between the human body and the clothes. Accordingly, even when the ultrasonic probe is attached to the human body for a long period of time, it is possible to prevent the inconvenience of a trouble in usual life.

In the ultrasonic probe according to the present aspect, it is preferable that the second substrate includes a control circuit configured to control the plurality of ultrasonic elements, and the control circuit includes a driver configured to drive the plurality of ultrasonic elements to transmit the ultrasonic waves, and a signal processing unit configured to process a signal to be output when the ultrasonic waves are received by the plurality of ultrasonic elements.

Accordingly, the ultrasonic measurement can be performed by the ultrasonic probe alone. The terminal device does not require various circuits related to the ultrasonic measurement, and a general-purpose computer can be used as the terminal device.

In the ultrasonic probe according to the present aspect, it is preferable that an acoustic lens, which converges the ultrasonic waves output from the ultrasonic element array to a predetermined depth, is provided in the opening of the housing.

Accordingly, the ultrasonic waves output from the ultrasonic element can be converged on a predetermined focal point by the acoustic lens. Accordingly, delay driving for converging the ultrasonic waves is not required, and a circuit configuration related to driving of the ultrasonic probe can be simplified.

An ultrasonic system according to a second aspect of the present disclosure includes: the ultrasonic probe described above; and a terminal device communicably connected via the communication unit.

Accordingly, the ultrasonic probe and the terminal device can wirelessly communicate with each other, and a user can control the ultrasonic probe using the terminal device in a state where the ultrasonic probe is attached to the target. At this time, since the ultrasonic probe and the terminal device are not coupled to each other by wire, it is possible to prevent an inconvenience caused by falling off of the ultrasonic probe due to wire catching and the like or a wire becomes an obstacle during the attachment of the ultrasonic probe.

What is claimed is:

1. An ultrasonic probe attached to a target to perform ultrasonic measurement, the ultrasonic probe comprising:

three directions perpendicular to one another being defined as an X direction, a Y direction, and a Z direction;

a housing provided with an opening facing along the Z direction;

a first substrate housed in the housing, the first substrate including an ultrasonic element array in which a plurality of ultrasonic elements performing at least one of transmission of ultrasonic waves and reception of ultrasonic waves are arranged in an array, the first substrate being configured with:

an ultrasonic substrate having first and second surfaces opposite to each other, each of the first and second surfaces extending along an X-Y plane, the X-Y plane extending along the X direction and the Y direction, the first surface facing the opening of the housing along the Z direction, the plurality of ultrasonic elements being provided on the second surface, the ultrasonic substrate having a plurality of partition walls on the first surface, each of the plurality of partition walls extending along the Z direction and being located between two adjacent ultrasonic elements of the plurality of ultrasonic elements via the ultrasonic substrate when viewed in a cross section, the cross section being along a Y-Z plane, the Y-Z plane extending along the Y direction and the Z direction, the ultrasonic waves passing through the opening of the housing; and a device substrate having third and fourth surfaces, each of the third and fourth surfaces extending along the X-Y plane, the device substrate having a plurality of legs that are formed on the third surface of the device substrate and are bonded to the second surface of the ultrasonic substrate at a plurality of positions to form a plurality of inner spaces between the second surface and the third surface when viewed in the cross section, each of the plurality of legs extending along the Z direction, the plurality of positions being aligned with the plurality of partition walls via the ultrasonic substrate when viewed in the cross section; and a second substrate housed in the housing, the second substrate facing the fourth surface of the device substrate along the Z direction, wherein the second substrate includes a communication interface and a battery, the communication interface and the battery are disposed on the same plane of the second substrate, and the communication interface is coupled to the plurality of ultrasonic elements and is configured to communicate wirelessly with another terminal device, a weight of the ultrasonic probe is 150 g or less, and the ultrasonic substrate is located closer to the opening of the housing than the device substrate.

2. The ultrasonic probe according to claim 1, wherein a dimension of the housing along the Z direction is 10 mm or less.

3. The ultrasonic probe according to claim 1, wherein the second substrate includes a control circuit configured to control the plurality of ultrasonic elements, and the control circuit includes a driver circuit configured to drive the plurality of ultrasonic elements to transmit the ultrasonic waves, and a signal processing circuit configured to process a signal to be output when the ultrasonic waves are received by the plurality of ultrasonic elements.

4. The ultrasonic probe according to claim 1, wherein an acoustic lens, which converges the ultrasonic waves received from the ultrasonic element array to a predetermined depth, is provided in the opening of the housing.

5. The ultrasonic probe according to claim 2, wherein the second substrate includes a control circuit configured to control the plurality of ultrasonic elements, and the control circuit includes a driver circuit configured to drive the plurality of ultrasonic elements to transmit the ultrasonic waves, and a signal processing circuit configured to process a signal to be output when the ultrasonic waves are received by the plurality of ultrasonic elements.

6. The ultrasonic probe according to claim 5, wherein an acoustic lens, which converges the ultrasonic waves received from the ultrasonic element array to a predetermined depth, is provided in the opening of the housing.

7. An ultrasonic system comprising:

an ultrasonic probe attached to a target to perform ultrasonic measurement, the ultrasonic probe including:

three directions perpendicular to one another being defined as an X direction, a Y direction, and a Z direction;

a housing provided with an opening facing along the Z direction;

a first substrate housed in the housing, the first substrate including an ultrasonic element array in which a plurality of ultrasonic elements performing at least one of transmission of ultrasonic waves and reception of ultrasonic waves are arranged in an array, the first substrate being configured with:

an ultrasonic substrate having first and second surfaces opposite to each other, each of the first and second surfaces extending along an X-Y plane, the X-Y plane extending along the X direction and the Y direction, the first surface facing the opening of the housing along the Z direction, the plurality of ultrasonic elements being provided on the second surface, the ultrasonic substrate having a plurality of partition walls on the first surface, each of the plurality of partition walls extending along the Z direction and being located between two adjacent ultrasonic elements of the plurality of ultrasonic elements via the ultrasonic substrate when viewed in a cross section, the cross section being along a Y-Z plane, the Y-Z plane extending along the Y direction and the Z direction, the ultrasonic waves passing through the opening of the housing; and a device substrate having third and fourth surfaces, each of the third and fourth surfaces extending along the X-Y plane, the device substrate having a plurality of legs that are formed on the third surface of the device substrate and are bonded to the second surface of the ultrasonic substrate at a plurality of positions to form a plurality of inner spaces between the second surface and the third surface when viewed in the cross section, each of the plurality of legs extending along the Z direction, the plurality of positions being aligned with the plurality of partition walls via the ultrasonic substrate when viewed in the cross section; and a second substrate housed in the housing, the second substrate facing the fourth surface of the device substrate along the Z direction; and a terminal device communicably connected via a communication interface, wherein the second substrate includes the communication interface and a battery, the communication interface and the battery are disposed on the same plane of the second substrate, and the communication interface is coupled to the plurality of ultrasonic elements and is configured to communicate wirelessly with the terminal device, a weight of the ultrasonic probe is 150 g or less, and the ultrasonic substrate is located closer to the opening of the housing than the device substrate.

8. The ultrasonic system according to claim 7, wherein a dimension of the housing along the X direction is 10 mm or less.

9. The ultrasonic system according to claim 7, wherein the second substrate includes a control circuit configured to control the plurality of ultrasonic elements, and the control circuit includes a driver circuit configured to drive the plurality of ultrasonic elements to transmit the ultrasonic waves, and a signal processing circuit configured to process a signal to be output when the ultrasonic waves are received by the plurality of ultrasonic elements.

10. The ultrasonic system according to claim 7, wherein an acoustic lens, which converges the ultrasonic waves received from the ultrasonic element array to a predetermined depth, is provided in the opening of the housing.

11. The ultrasonic system according to claim 8, wherein the second substrate includes a control circuit configured to control the plurality of ultrasonic elements, and the control circuit includes a driver circuit configured to drive the plurality of ultrasonic elements to transmit the ultrasonic waves, and a signal processing circuit configured to process a signal to be output when the ultrasonic waves are received by the plurality of ultrasonic elements.

12. The ultrasonic system according to claim 11, wherein an acoustic lens, which converges the ultrasonic waves received from the ultrasonic element array to a predetermined depth, is provided in the opening of the housing.

* * * * *